United States Patent [19]

Okushima et al.

[11] Patent Number: 5,053,409

[45] Date of Patent: Oct. 1, 1991

[54] AMINOBENZENESULFONIC ACID DERIVATIVES

[75] Inventors: Hiromi Okushima, Kawasaki; Akihiro Narimatsu, Yokohama; Makio Kobayashi, Machida; Naoya Satoh; Miyuki Morita, both of Yokohama, all of Japan

[73] Assignee: Mitsubishi Kasei Corporation, Tokyo, Japan

[21] Appl. No.: 497,184

[22] Filed: Mar. 22, 1990

[30] Foreign Application Priority Data

Mar. 27, 1989 [JP] Japan ................................. 1-74684

[51] Int. Cl.$^5$ .................. A61K 31/495; C07D 295/02; C07D 295/06; C07D 295/08
[52] U.S. Cl. ..................... 514/255; 514/218; 540/450; 540/575; 544/392; 544/394; 544/395
[58] Field of Search ................. 540/575, 450; 544/395, 544/394, 392; 514/255, 218

[56] References Cited

U.S. PATENT DOCUMENTS 2,976,290  3/1961  Parcell ................................. 544/395
3,007,928  11/1961 Parcell ................................. 544/395
3,028,390  4/1962  Parcell ................................. 544/394
3,262,852  7/1966  Servier et al. ....................... 544/394
3,951,986  4/1976  Maruyama et al. ................. 544/394

Primary Examiner—Cecelia Shen
Attorney, Agent, or Firm—Oblon, Spivak, McClelland, Maier & Neustadt

[57] ABSTRACT

There is disclosed an aminobenzenesulfonic acid derivative of the formula:

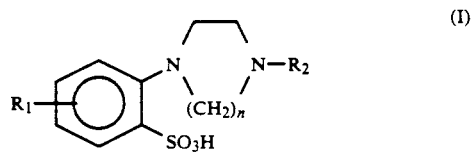

wherein $R_1$ represents hydrogen atom, a $C_1$–$C_6$ alkyl group, a $C_3$–$C_7$ cycloalkyl group, a $C_1$–$C_4$ halogenated alkyl group, a halogen atom or a $C_6$–$C_{12}$ aryl group, $R_2$ represents hydrogen atom, a $C_1$–$C_6$ alkyl group or a $C_7$–$C_{12}$ aralkyl group which may have at least one substituent selected from cyano group, nitro group, $C_1$–$C_6$ alkoxy groups, halogen atoms, $C_1$–$C_6$ alkyl groups and amino groups, and n represents an integer of 1 to 4, of a pharmaceutically acceptable salt thereof.

24 Claims, No Drawings

AMINOBENZENESULFONIC ACID DERIVATIVES

BACKGROUND OF THE INVENTION

This invention relates to novel aminobenzenesulfonic acid derivatives having the activity of inhibiting $Ca^{2+}$ overload into cells.

$Ca^{2+}$ overload into cells of cardiac muscle or vascular smooth muscle brings about myocardial disorder, conduction disorder or vascular abnormal constriction, etc., and may induce cardiovascular diseases (John A. Watts, American Journal of Physiology, Vol. 238, pp. 909-916 (1980) or Gordon L. Todd, Cardiovascular Research, Vol. 20, pp. 645-651 (1986)).

Therefore, drugs which inhibit $Ca^{2+}$ overload into these cells can be useful prophylactic and therapeutical pharmaceuticals for cardiovascular diseases such as ischemic heart diseases, heart failure, hypertension or arrhythmia, etc.

In the prior art, as the drug for inhibiting $Ca^{2+}$ overload into cells of cardiac muscle or vascular smooth muscle, there have been known, for example, Ca antagonists or $\beta$-adrenoceptor antagonists. However, these drugs, depending on their doses used, have been known to inhibit cardiac function by lowering $Ca^{2+}$ concentration within cells in the case of Ca antagonists, or by blocking catecholamine activity in the case of $\beta$-blockers, thereby inducing heart failure (Keiji Ueda, Sogo Rinsho, Vol. 36, pp. 851-854 (1987)), and therefore the application to cardiovascular diseases has been limited.

SUMMARY OF THE INVENTION

The present inventors have intensively searched for compounds which inhibit $Ca^{2+}$ overload into cells, and consequently found novel compounds which inhibit $Ca^{2+}$ overload into cells without side-effect on cardiovascular systems to accomplish the present invention.

More specifically, the characteristic feature of the present invention resides in an aminobenzenesulfonic acid derivative of the formula:

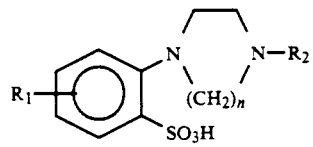

wherein $R_1$ represents hydrogen atom, a $C_1$–$C_6$ alkyl group, a $C_3$–$C_7$ cycloalkyl group, a $C_1$–$C_4$ halogenated alkyl group, a halogen atom or a $C_6$–$C_{12}$ aryl group, $R_2$ represents hydrogen atom, a $C_1$–$C_6$ alkyl group or a $C_7$–$C_{12}$ aralkyl group which may also have at least one substituent selected from cyano group, nitro group, $C_1$–$C_6$ alkoxy groups, halogen atoms, $C_1$–$C_6$ alkyl groups and amino group, and n represents an integer of 1 to 4, or a pharmaceutically acceptable salt thereof.

DESCRIPTION OF THE PREFERRED EMBODIMENTS

As $R_1$, there may be included hydrogen atom, a $C_1$–$C_6$ straight or branched alkyl group such as methyl, ethyl, n-propyl, iso-propyl, n-butyl, t-butyl, n-pentyl and n-hexyl groups, a $C_3$–$C_7$ cycloalkyl group such as cyclopropyl, cyclobutyl, cyclopentyl and cyclohexyl groups, a $C_1$–$C_4$ halogenated alkyl group such as trifluoromethyl group, a halogen atom such as fluorine, chlorine and bromine atoms or a $C_6$–$C_{12}$ aryl group such as phenyl, tolyl and naphthyl groups; and, as $R_2$, there may be included hydrogen atom; a $C_1$–$C_6$ straight or branched alkyl group such as methyl, ethyl, n-propyl, iso-propyl, n-butyl, t-butyl, n-pentyl and n-hexyl groups; a $C_7$–$C_{12}$ aralkyl group such as benzyl, phenethyl and naphthylmethyl groups, which may also have at least one substituent selected from cyano group, nitro group, $C_1$–$C_6$ alkoxy groups such as methoxy, ethoxy, propoxy, butoxy pentoxy and hexyloxy groups, halogen atoms such as fluorine, chlorine and bromine atoms, $C_1$–$C_6$ straight or branched alkyl group such as methyl, ethyl, n-propyl, iso-propyl, n-butyl, t-butyl, n-pentyl and n-hexyl groups, and amino group.

As specific compounds of the present invention, for example, those set forth in the following Table 1 may be included.

TABLE 1

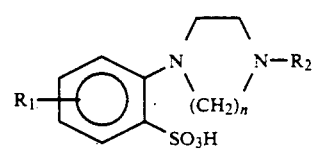

| Compound No. | Substitution position of $R_1$ | $R_1$ | n | $R_2$ |
|---|---|---|---|---|
| 1 | — | H | 2 | H |
| 2 | 3 | —$CH_3$ | 2 | H |
| 3 | 3 | —$CH_2CH_3$ | 2 | H |
| 4 | 3 | —$CH_2CH_2CH_3$ | 2 | H |
| 5 | 3 | —$CH(CH_3)_2$ | 2 | H |
| 6 | 3 | —$(CH_2)_3CH_3$ | 2 | H |
| 7 | 4 | —$CH_3$ | 2 | H |
| 8 | 4 | —$CH_2CH_3$ | 2 | H |
| 9 | 4 | —$(CH_2)_2CH_3$ | 2 | H |
| 10 | 4 | —$CH(CH_3)_2$ | 2 | H |
| 11 | 4 | —$(CH_2)_3CH_3$ | 2 | H |
| 12 | 5 | —$CH_3$ | 2 | H |
| 13 | 5 | —$CH_2CH_3$ | 2 | H |
| 14 | 5 | —$CH_2CH_2CH_3$ | 2 | H |
| 15 | 5 | —$CH(CH_3)_2$ | 2 | H |
| 16 | 5 | —$(CH_2)_3CH_3$ | 2 | H |

TABLE 1-continued (I)

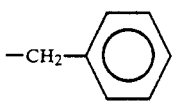

| Compound No. | Substitution position of $R_1$ | $R_1$ | n | $R_2$ |
|---|---|---|---|---|
| 17 | 5 | —(CH$_2$)$_4$CH$_3$ | 2 | H |
| 18 | 5 | —(CH$_2$)$_5$CH$_3$ | 2 | H |
| 19 | 6 | —CH$_3$ | 2 | H |
| 20 | 6 | —CH$_2$CH$_3$ | 2 | H |
| 21 | 6 | —(CH$_2$)$_2$CH$_3$ | 2 | H |
| 22 | — | H | 2 | —CH$_3$ |
| 23 | 3 | —CH$_2$CH$_3$ | 2 | —CH$_3$ |
| 24 | 3 | —(CH$_2$)$_2$CH$_3$ | 2 | —CH$_3$ |
| 25 | 3 | —CH(CH$_3$)$_2$ | 2 | —CH$_3$ |
| 26 | 3 | —(CH$_2$)$_3$CH$_3$ | 2 | —CH$_3$ |
| 27 | 4 | —CH$_3$ | 2 | —CH$_3$ |
| 28 | 4 | —CH$_2$CH$_3$ | 2 | —CH$_3$ |
| 29 | 4 | —(CH$_2$)$_2$CH$_3$ | 2 | —CH$_3$ |
| 30 | 5 | —CH$_3$ | 2 | —CH$_3$ |
| 31 | 5 | —CH$_2$CH$_3$ | 2 | —CH$_3$ |
| 32 | 5 | —(CH$_2$)$_2$CH$_3$ | 2 | —CH$_3$ |
| 33 | 5 | —CH(CH$_3$)$_2$ | 2 | —CH$_3$ |
| 34 | 5 | —(CH$_2$)$_3$CH$_3$ | 2 | —CH$_3$ |
| 35 | 5 | —(CH$_2$)$_4$CH$_3$ | 2 | —CH$_3$ |
| 36 | 5 | —(CH$_2$)$_5$CH$_3$ | 2 | —CH$_3$ |
| 37 | 6 | —CH$_3$ | 2 | —CH$_3$ |
| 38 | 6 | —CH$_2$CH$_3$ | 2 | —CH$_3$ |
| 39 | 6 | —(CH$_2$)$_2$CH$_3$ | 2 | —CH$_3$ |
| 40 | 6 | —CH(CH$_3$)$_2$ | 2 | —CH$_3$ |
| 41 | 6 | —(CH$_2$)$_3$CH$_3$ | 2 | —CH$_3$ |
| 42 | 3 | —(CH$_2$)$_2$CH$_3$ | 2 | —(CH$_2$)$_2$CH$_3$ |
| 43 | 4 | —(CH$_2$)$_2$CH$_3$ | 2 | —(CH$_2$)$_2$CH$_3$ |
| 44 | 5 | —CH$_3$ | 2 | —(CH$_2$)$_2$CH$_3$ |
| 45 | 5 | —CH$_2$CH$_3$ | 2 | —(CH$_2$)$_2$CH$_3$ |
| 46 | 5 | —(CH$_2$)$_2$CH$_3$ | 2 | —(CH$_2$)$_2$CH$_3$ |
| 47 | 5 | —CH(CH$_3$)$_2$ | 2 | —(CH$_2$)$_2$CH$_3$ |
| 48 | 5 | —(CH$_2$)$_3$CH$_3$ | 2 | —(CH$_2$)$_2$CH$_3$ |
| 49 | 5 | —(CH$_2$)$_5$CH$_3$ | 2 | —(CH$_2$)$_2$CH$_3$ |
| 50 | — | H | 2 | —(CH$_2$)$_2$CH$_3$ |
| 51 | — | H | 2 | 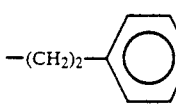 |
| 52 | 3 | —CH$_3$ | 2 | 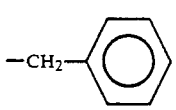 |
| 53 | 3 | —(CH$_2$)$_2$CH$_3$ | 2 | 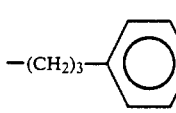 |
| 54 | 4 | —CH$_3$ | 2 | 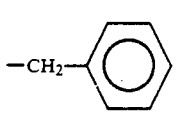 |
| 55 | 4 | —(CH$_2$)$_2$CH$_3$ | 2 | 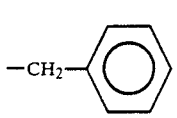 |
| 56 | 5 | —CH$_3$ | 2 |  |

TABLE 1-continued
(I)
| Compound No. | Substitution position of $R_1$ | $R_1$ | n | $R_2$ |
|---|---|---|---|---|
| 57 | 5 | —$CH_2CH_3$ | 2 | —$CH_2$—⌬ |
| 58 | 5 | —$(CH_2)_2CH_3$ | 2 | —$CH_2$—⌬ |
| 59 | 5 | —$CH(CH_3)_2$ | 2 | —$CH_2$—⌬ |
| 60 | 5 | —$(CH_2)_3CH_3$ | 2 | —$CH_2$—⌬ |
| 61 | 5 | —$(CH_2)_4CH_3$ | 2 | —$(CH_2)_3$—⌬ |
| 62 | 5 | —$(CH_2)_2CH_3$ | 2 | —$CH_2$—⌬—$OCH_3$ |
| 63 | 5 | —$CH(CH_3)_2$ | 2 | —$CH_2$—⌬—$OCH_3$ (meta) |
| 64 | 5 | —$CH(CH_3)_2$ | 2 | —$CH_2$—⌬—$OCH_3$ (ortho) |
| 65 | 4 | —$(CH_2)_2CH_3$ | 2 | —$(CH_2)_4$—⌬($OCH_3$)$_2$ |
| 66 | 5 | —$(CH_2)_2CH_3$ | 2 | —$CH_2$—⌬($OCH_3$)$_2$ |

TABLE 1-continued (I)

R₁–[benzene ring with SO₃H]–N[piperazine ring (CH₂)ₙ]N–R₂

| Compound No. | Substitution position of R₁ | R₁ | n | R₂ |
|---|---|---|---|---|
| 67 | 5 | —CH(CH₃)₂ | 2 | —(CH₂)₂—[phenyl]—OCH₃ (with OCH₃) |
| 68 | 6 | —(CH₂)₂CH₃ | 2 | —CH₂—[phenyl]—OCH₃ (with OCH₃) |
| 69 | 5 | —(CH₂)₂CH₃ | 2 | —CH₂—[phenyl with OCH₃, OCH₃, H₃CO] |
| 70 | 6 | —(CH₂)₂CH₃ | 2 | —CH₂—[phenyl with OCH₃, OCH₃, H₃CO] |
| 71 | 3 | —(CH₂)₂CH₃ | 2 | —CH₂—[phenyl]—CH₃ |
| 72 | 4 | —(CH₂)₂CH₃ | 2 | —(CH₂)₂—[phenyl]—CH₃ |
| 73 | 5 | —(CH₂)₂CH₃ | 2 | —CH₂—[phenyl]—CH₃ |
| 74 | 6 | —CH(CH₃)₂ | 2 | —CH₂—[phenyl]—CH₃ |
| 75 | 3 | —(CH₂)₂CH₃ | 2 | —CH₂—[phenyl]—Cl |
| 76 | 4 | —(CH₂)₂CH₃ | 2 | —CH₂—[phenyl]—Cl |
| 77 | 5 | —(CH₂)₂CH₃ | 2 | —CH₂—[phenyl]—Cl |

TABLE 1-continued $$\underset{R_1}{\overset{}{\bigcirc}}\underset{SO_3H}{\overset{N}{\underset{(CH_2)_n}{\bigvee}}}\overset{N-R_2}{\underset{}{\bigg)}}\quad (I)$$

| Compound No. | Substitution position of $R_1$ | $R_1$ | n | $R_2$ |
|---|---|---|---|---|
| 78 | 6 | $-(CH_2)_2CH_3$ | 2 | $-CH_2-\bigcirc-Cl$ |
| 79 | 3 | $-(CH_2)_2CH_3$ | 2 | $-CH_2-\bigcirc-OCH_3$ |
| 80 | 4 | $-(CH_2)_2CH_3$ | 2 | $-CH_2-\bigcirc-OCH_3$ |
| 81 | 5 | $-(CH_2)_2CH_3$ | 2 | $-(CH_2)_2-\bigcirc-OCH_3$ |
| 82 | 6 | $-(CH_2)_2CH_3$ | 2 | $-CH_2-\bigcirc-OCH_3$ |
| 83 | — | H | 3 | H |
| 84 | 5 | $-CH_3$ | 3 | H |
| 85 | 5 | $-CH_2CH_3$ | 3 | H |
| 86 | 5 | $-(CH_2)_2CH_3$ | 3 | H |
| 87 | 5 | $-CH(CH_3)_2$ | 3 | H |
| 88 | 5 | $-(CH_2)_3CH_3$ | 3 | H |
| 89 | 5 | $-(CH_2)_2CH_3$ | 3 | $-CH_3$ |
| 90 | 5 | $-(CH_2)_2CH_3$ | 3 | $-\bigcirc\genfrac{}{}{0pt}{}{-OCH_3}{-OCH_3}$ |
| 91 | 5 | $-\bigcirc$ | 2 | H |
| 92 | 5 | $-F$ | 2 | H |
| 93 | 5 | $-Cl$ | 2 | H |
| 94 | 5 | $-Br$ | 2 | H |
| 95 | 5 | $-CF_3$ | 2 | H |
| 96 | 5 | cyclohexyl | 2 | H |
| 97 | 5 | cyclopentyl | 2 | H |

TABLE 1-continued
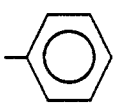
(I)
| Compound No. | Substitution position of $R_1$ | $R_1$ | n | $R_2$ |
|---|---|---|---|---|
| 98 | 5 | 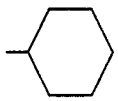 | 2 | —$CH_3$ |
| 99 | 5 | —Cl | 2 | —$CH_3$ |
| 100 | 5 | —Br | 2 | —$CH_3$ |
| 101 | 5 | —$CF_3$ | 2 | —$CH_3$ |
| 102 | 5 |  | 2 | —$CH_3$ |
| 103 | 5 | 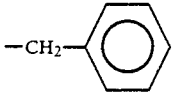 | 2 | —$CH_3$ |
| 104 | 5 | 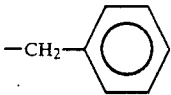 | 2 | —$CH_2$—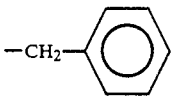 |
| 105 | 5 | —Cl | 2 | —$CH_2$—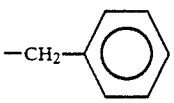 |
| 106 | 5 | —Br | 2 | —$CH_2$—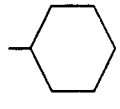 |
| 107 | 5 | —$CF_3$ | 2 | —$CH_2$— |
| 108 | 5 |  | 2 | —$CH_2$— |
| 109 | 5 | 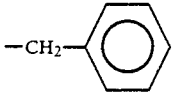 | 2 | —$CH_2$— |
| 110 (hydrochloride of Compound No. 14) | 5 | —$CH_2CH_2CH_3$ | 2 | H |
| 111 (hydrochloride of Compound No. 15) | 5 | —$CH(CH_3)_2$ | 2 | H |
| 112 (hydrochloride of Compound No. 96) | 5 | 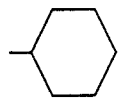 | 2 | H |

Also, the pharmaceutically acceptable salts of the above compounds are also included within the scope of the present invention.

The above salts are nontoxic salts such as alkali metal salts or alkaline earth metal salts, as exemplified by sodium salts, potassium salts, magnesium salts, calcium salts and aluminum salts. Adequate nontoxic amine salts such as ammonium salts, lower alkylamine [e.g. triethylamine] salts, hydroxy lower alkylamine [e.g. 2-hydroxyethylamine, bis-(2-hydroxyethyl)amine, tris-(hydroxymethyl)aminomethane or N-methyl-D-glucamine] salts, cycloalkylamine [e.g. dicyclohexylamine] salts, benzylamine [e.g. N,N-dibenzylethylenediamine] salts and dibenzylamine salts are also similarly preferred.

When calling attention on the heterocyclic ring containing two nitrogens included in the compounds of the present invention, preferred salts may include nontoxic salts such as hydrochlorides, hydrobromides, sulfates, phosphates, fumarates, succinates, oxalates and lactates.

When the compound according to the present invention is used as a drug for cardiovascular system, it is adapted orally or parenterally to human in conventional manner. As the dosage form for oral administration, there may be included granules, fine granules, powders, tablets, hard capsules, soft capsules, syrups, emulsions, suspensions and solutions. As the dosage form for parenteral administration, injections, suppositories and percutaneous agents, may be included.

The compound represented by the above formula (I) or its pharmaceutically acceptable salt is contained in the above dosage form together with a solid or liquid carrier for pharmaceutical or an additive for pharmaceutical such as excipient, stabilizer, lubricant, sweetener, preservative and suspending agent, and the ratio of the active ingredient in therapy based on the carrier component should be preferably within the range from 1% by weight to 90% by weight.

Examples of solid carriers to be used may include lactose, kaolin, sucrose, crystalline cellulose, corn starch, talc, agar, pectin, acacia, stearic acid, magnesium stearate, lecithin and sodium chloride. Examples of liquid carriers may include syrup, glycerin, peanut oil, polyvinyl pyrrolidone, olive oil, ethanol, benzyl alcohol, propylene glycol and water.

When the compound of the present invention is used orally, its amount used may be within the range from 0.01 mg to 1000 mg (preferably from 0.1 mg to 100 mg) for human adult per day, but more preferably be increased or decreased suitably depending on the age, sex, condition, symptom, and presence of simultaneous treatment. The number of administration may be once per day, or in several divided doses per day with appropriate intervals.

When the compound of the present invention is used as an injection agent, it should be preferably administered continuously or intermittently for human adult in an amount of 0.01 mg to 100 mg per dose.

In the following, the method for preparing the compound of the present invention is to be described.

The compound of the present invention can be prepared according to, for example, the following route (1).

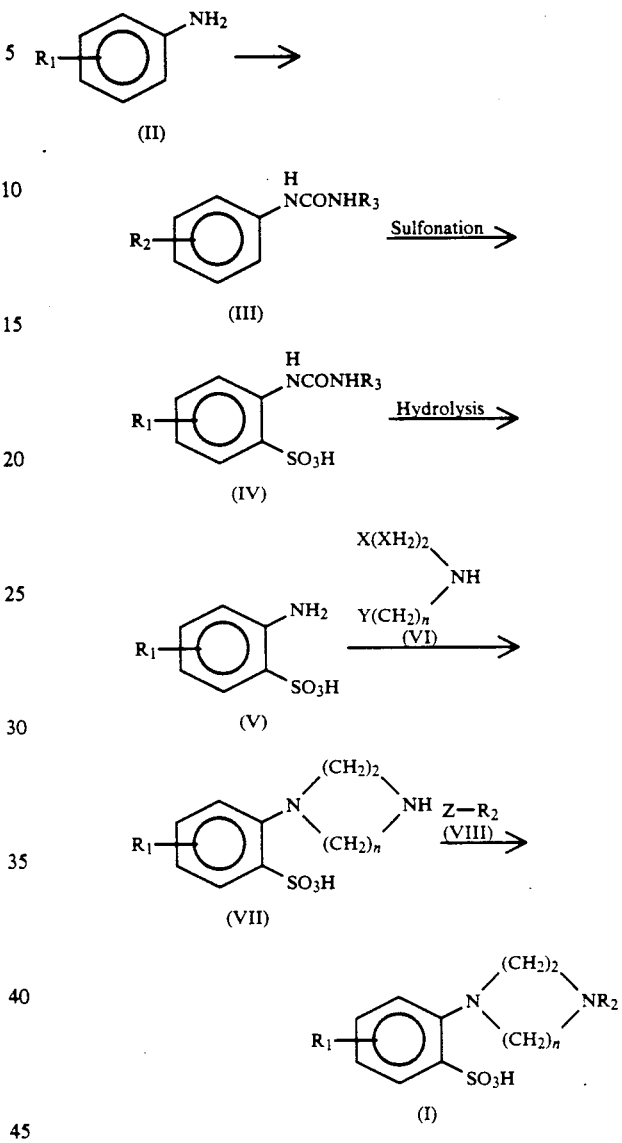

(In the above formulae, $R_1$, $R_2$ and n are as already defined, $R_3$ represents hydrogen atom or a $C_1$–$C_6$ lower alkyl group, X and Y each independently represent a halogen atom, and Z represents a halogen atom or

By reacting the aniline represented by the above formula (II) with an isocyanic acid or a salt of isocyanic acid such as sodium isocyanate, in a polar solvent such as acetic acid or a solvent mixture of acetic acid and water at 0° C. to 100° C. for several minutes to several hours, or by reacting the aniline represented by the above formula (II) with an isocyanic acid ester such as methyl isocyanate and ethyl isocyanate in an organic solvent such as ethyl acetate, tetrahydrofuran, N,N-dimethylformamide, toluene, hexane, diethyl ether and acetone, or a mixture thereof at 0° C. to 100° C. for several minutes to several hours, the urea compound represented by the above formula (III) can be obtained.

By reacting the urea compound (III) obtained by the above reaction with conc. sulfuric acid, fuming sulfuric acid, anhydrous sulfuric acid or chlorosulfonic acid at −20° C. to 100° C. for several minutes to several hours, the ureidobenzenesulfonic acid represented by the above formula (IV) can be obtained.

By hydrolyzing the ureidobenzenesulfonic acid (IV) obtained by the above reaction in an aqueous solution of hydrochloric acid, sulfuric acid or sodium hydroxide, at room temperature to 150° C. for several minutes to several hours, the aminobenzenesulfonic acid represented by the above formula (V) can be obtained.

By heating the aminobenzenesulfonic acid (V) obtained by the above reaction together with the amine represented by the above formula (VI) in a polar solvent such as water, ethanol, N,N-dimethylformamide or dimethyl sulfoxide, at 50° to 200° C. for several minutes to several hours, the cyclic aminobenzenesulfonic acid represented by the above formula (VII) can be obtained. In this case, if necessary, an appropriate amount of a base such as sodium hydroxide and triethylamine, may be also added for neutralizing the acid component formed during the reaction.

By heating the cyclic aminobenzenesulfonic acid (VII) obtained by the above reaction together with the halide compound represented by the above formula (VIII) (wherein Z represents a halogen atom) in a polar solvent such as water, ethanol or N,N-dimethylformamide, at room temperature to 150° C. for several minutes to several hours, the aminobenzenesulfonic acid represented by the above formula (I) which is the compound of the present invention can be obtained.

When the compound represented by the above formula (VIII) is an aldehyde compound (wherein Z represents

said aldehyde compound and the cyclic aminobenzenesulfonic acid (VII) obtained by the above reaction may be hydrogenated in conventional manner in a polar solvent such as methanol, ethanol, acetic acid, dimethylformamide and water, in the presence of a catalyst such as palladium, to carry out reductive amination reaction, or the above aldehyde compound (VIII) and the above cyclic aminobenzenesulfonic acid (VII) may be subjected to the reaction in the above polar solvent with addition of a reducing agent such as sodium cyanoborohydride at 0° to 100° C. for several minutes to several hours to carry out reductive amination reaction, whereby the aminobenzenesulfonic acid (I) which is the compound of the present invention can be also obtained. Also, the cyclic aminobenzenesulfonic acid represented by the above formula (VII) can be also prepared according to the following route (2).

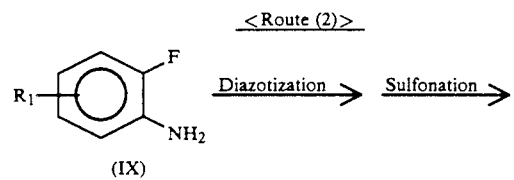

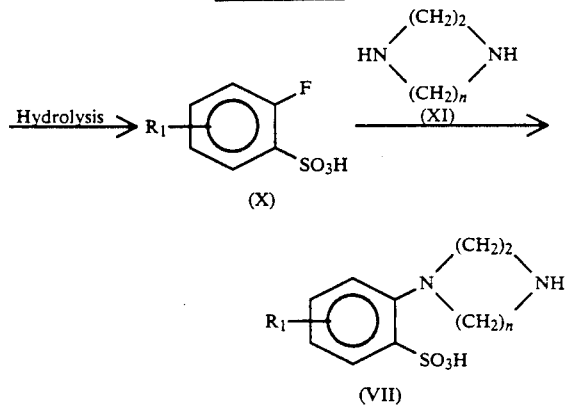

By diazotizing the o-fluoroaniline represented by the above formula (IX) with a nitrite such as sodium nitrite in an acid such as hydrochloric acid and sulfuric acid, at −20° to 10° C., subsequently reacting the reaction product with sulfur dioxide in a polar solvent such as acetic acid and dioxane, at −20° to 40° C. to convert it to a sulfonyl chloride, and hydrolyzing this in water, ethanol, methanol or a solvent mixture thereof in the presence of a strong alkali such as sodium hydroxide, the o-fluorosulfonic acid represented by the above formula (X) can be obtained.

By heating the o-fluorosulfonic acid (X) obtained by this reaction together with the cyclic diamine represented by the above formula (XI) in a polar solvent such as N,N-dimethylformamide or without solvent, occasionally in the presence of a catalyst such as copper powder and copper iodide, at 50° to 200° C. for several hours to several tens of hours, the cyclic aminobenzenesulfonic acid represented by the above formula (VII) can be obtained.

EXAMPLES

The present invention is described in more detail below by referring to Examples, but the present invention, within its spirit, is not limited by the following Examples at all. And Compound No. in the following Examples corresponds to Compound No. in Table 1 as mentioned above.

Reference example 1

Synthesis of 2-amino-5-n-propylbenzenesulfonic acid

A solution of 31.4 g of p-n-propylaniline dissolved in 116 ml of acetic acid and 232 ml of water was added dropwise into 200 ml of a mixed solution comprising 130 g of sodium isocyanate and 900 ml of water, and then stirred in an ice-bath for 30 minutes. The crystals precipitated were filtered, washed with water and dried to give 38.88 g of 4-n-propylphenylurea. After the 4-n-propylphenylurea was added in portions into 107.6 ml of 20% fuming sulfuric acid, the reaction was carried out at 60° C. for 2 hours. Under cooling in an ice-bath, about 400 ml of ice was added into the reaction mixture, followed by heating under reflux for 4 hours. The crystals precipitated by cooling were filtered, washed with water and then dried to give 30.09 g of the above title product (yield: 64.1%). Melting point: 30 261.7°–262.3° C.

Reference example 2

Synthesis of 2-fluoro-5-n-propylbenzenesulfonic acid

A solution of 12.53 g of 2-fluoro-5-n-propylaniline dissolved in a mixed solution of 73 ml of conc. sulfuric acid and 120 ml of water was cooled to −10° C. and an aqueous sodium nitrite solution containing 6.15 g of sodium nitrite dissolved in 15 ml of water was added dropwise thereinto at a temperature of −5° C. or lower, followed by stirring at this temperature for 25 minutes to prepare a diazonium salt solution. The diazonium salt solution was added dropwise into a mixed solution of 120 ml of acetic acid saturated with sulfur dioxide and 2.92 ml of copper chloride dissolved in 20 ml of water at a temperature of −20° C., and after stirred at −10° C. for 30 minutes and further at 0° C. for one hour, the oily substance separated was extracted with ethyl acetate. Ethyl acetate was evaporated under reduced pressure from the extract, and to the residue were added 90 ml of 2 N sodium hydroxide solution and 200 ml of dioxane. After the mixture was heated at 100° C. for 5 minutes, it was neutralized with acetic acid and the reaction product was purified by silica gel chromatography (eluant:-chloroform:methanol:acetic acid =500:50:6) to give 7.13 g (yield: 39.9%) of the above title compound as a paste.

NMR (DMSO-d$_6$) δ ppm: 0.868 (t, 3H), 1.536 (m, 2H), 2.51 (t, 2H), 7.00 (q, 1H), 7.155 (m, 1H), 7.468 (dd, 1H).

EXAMPLE 1

Synthesis of 2-(1-piperazinyl)-5-methylbenzenesulfonic acid (Compound No. 12)

After the reaction was carried out between 0.76 g of 2-fluoro-5-methylbenzenesulfonic acid and 3.44 g of piperazine in the co-presence of 0.76 g of copper iodide and 0.26 g of copper powder in a sealed tube at 160° C. for 8 hours, the reaction product was purified by silica gel column chromatography (eluant:chloroform:methanol:acetic acid =100:100:3) to give 0.67 g (yield: 65.0%) of the above title product having the following physical property.

Melting point: 271° C. (decomposed).

In the same manner as mentioned above, Compound No. 95 was obtained (yield: 33.7%).

Melting point: 300° C. or higher.

EXAMPLE 2

Synthesis of 2-(1-piperazinyl)-5-n-propylbenzenesulfonic acid (Compound No. 14)

To 500 ml of water are added 50.0 g of 2-amino-5-n-propylbenzenesulfonic acid and 6.28 g of sodium carbonate and the mixture was dissolved by heating. To the solution was added 88.13 g of bis(2-chloroethyl)amine hydrochloride and the mixture was refluxed by heating for 3 hours, And then, a suspension containing 26.25 g of sodium carbonate suspended in 63 ml of water was added thereto, and the mixture was refluxed by heating for 12 hours. The reaction mixture was condensed under reduced pressure, extracted with methyl alcohol and then methyl alcohol was removed under reduced pressure. To the residue was added 200 ml of water, and after a pH of the mixture was adjusted to about 8.0 with sodium carbonate, 500 ml of chloroform was added thereto and the mixture was stirred. Precipitated crystals were collected by filtration, washed with chloroform and dried to give 44.83 g (yield: 67.9%) of the above title product.

Melting point: 286° C. (decomposed).

In the same manner as mentioned above, the following compounds were obtained.

| Compound No. | Yield (%) | Melting point °C |
|---|---|---|
| 91 | 27.6 | 290 (decomposed) |
| 93 | 50.7 | 230 (decomposed) |
| 94 | 18.7 | 270 (decomposed) |

EXAMPLE 3

Synthesis of 2-(1-piperazinyl)-5-n-propylbenzenesulfonic acid hydrochloride (Compound No. 110)

To a mixed solution of 200 ml of ethyl alcohol and 185 ml of 1 N hydrochloric acid was added 50. g of 2-(1-piperazinyl)-5-n-propylbenzenesulfonic acid and the mixture was dissolved by heating. The mixture was condensed under reduced pressure, and precipitated crystals were washed with acetone and dried to give 51.46 g (yield: 95.4%) of the above title product.

Melting point: 275° C. (decomposed).

In the same manner as mentioned above, the following compounds were obtained.

| Compound No. | Melting point (°C.) |
|---|---|
| 111 | 220 (decomposed) |
| 112 | 225 (decomposed) |

EXAMPLE 4

Synthesis of 2-(1-homopiperazinyl)-5-n-propylbenzenesulfonic acid (Compound No. 86)

According to the same method as in Example 2, from 0.61 g of 2-fluoro-5-n-propylbenzenesulfonic acid and 2.80 g of homopiperazine, 0.31 g (yield: 37.2%) of the above title product having the following physical property was obtained.

Melting point: 205°–210° C. (decomposed).

EXAMPLE 5

Synthesis of 2-[4-(2,3,4-trimethoxybenzyl)-1-piperazinyl]-5-n-propylbenzenesulfonic acid (Compound No. 69)

Into a solution of 0.10 g of sodium cyanoborohydride dissolved in 2 ml of a methanol solution was added 0.1 g of zinc chloride, and the mixture was stirred for 5 minutes. Then, 0.40 g of 2-(1-piperazinyl)-5-n-propylbenzenesulfonic acid and 0.58 g of 2,3,4-trimethoxybenzaldehyde were added to carry out the reaction at room temperature for 2 hours. The organic layer was extracted by addition of an aqueous sodium chloride and tetrahydrofuran, and after evaporation of tetrahydrofuran under reduced pressure from the extract, the residue was purified by silicagel column chromatography (eluant:chloroform: methanol:acetic acid=500:100:6) to give 0.39 g (yield: 58.5%) of the above title product as a glassy solid.

Melting point: 175°–180° C. (decomposed)

NMR (DMSO-d6) δ ppm: 0.870 (t, 3H, J=7.4Hz), 1.529 (m, H), 2.458 (t, 2H, J=7.8Hz), 2.637 (broad m, 4H), 3.090 (broad m, 4H), 3.601 (broad s, 2H), 3.752 (s, 3H), 3.788 (s, 3H), 3.817 (s, 3H), 6.795 (d, 1H, J=8.7Hz), 6.909 (d, 1H, J=8Hz), 7.050 (d, 2H, J=8.7Hz), 7.638 (d, 1H, J=2.0Hz).

In the same manner as mentioned above, Compound No. 66 was obtained as a glassy solid (yield: 91.1%).

TEST EXAMPLE 1

For evaluation of the extent of inhibiting $Ca^{2+}$ overload into cells, which is the pharmacological activity of the compound of the present invention, inhibition of the cardiotonic activity of isoproterenol by the compounds of the present invention was measured.

That is to say, since isoproterenol has been known to cause $Ca^{2+}$ overload by excessive $Ca^{2+}$ influx into cardiac muscle cells (Fleckenstein A., Janke J., Doring H., Leder 0.; Recent advances in Studies on cardiac structure and metabolism, Myocardial Biology, Vol. 4, pp. 563-580 (1974)), the compound which inhibits the activity of isoproterenol can inhibit $Ca^{2+}$ overload into cells.

<Method>

Papillary muscle of right ventricle isolated from male Hartley-strain guinea-pigs (body weight: 250 to 350 g) was suspended in an organ bath filled with a nutrient solution (Krebs-Henseleit solution). The temperature of the nutrient solution was maintained at 32° C., and a gas mixture of 95% oxygen and 5% carbon dioxide was aerated. The papillary muscle was applied with a resting tension of about 0.5 g, and stimulated with platinum electrodes by an electric pulse wave of a duration of 1 msec, a frequency of 1 Hz and a voltage higher by 15% than the threshold value. The developed tension of the papillary muscle was measured through a tension transducer and recorded with a polygraph. After the specimen was stabilized for about 90 minutes, isoproterenol ($10^{-3}$ to $10^{-7}$ M) was added into the organ bath so that developed tension could be increased by 100% or more, and at the point when the maximum reaction was obtained, the compounds of the present invention were added into the organ bath, and % inhibition of the developed tension increased by isoproterenol was measured.

<Results>

The % inhibition of the respective compounds are shown in Table 2.

TABLE 2

| Compound No. | Inhibition (%) Drug concentration (M) | | |
|---|---|---|---|
| | $10^{-5}$ | $10^{-4}$ | $10^{-3}$ |
| 12 | — | — | 18.5 |
| 14 | 10.4 | 19.2 | — |
| 66 | — | — | 52.4 |
| 69 | — | — | 21.4 |
| 91 | — | — | 17.2 |
| 93 | — | — | 28.0 |
| 94 | — | — | 18.5 |
| 110 | 12.5 | 18.2 | 42.9 |
| 111 | — | — | 27.5 |

The compounds of the present invention have the activity of inhibiting $Ca^{2+}$ overload into cells of cardiac muscle or vascular smooth muscle, and therefore according to the present invention, there is provided novel aminobenzenesulfonic acid derivatives useful for prophylaxis and therapy of various cardiovascular diseases, such as angina pectoris, myocardial infarction, hypertension, heart failure or arrhythmia.

TEST EXAMPLE 2

Protective effect on ischemic myocardium

For the evaluation of the protective effect of ischemic myocardium, two parameters (rise in resting tension and decrease in developed tension), indices of myocardial injury, were measured in the myocardial ischemic model using isolated heart of rat.

It is reported that drugs which have the protective effect on ischemic myocardium attenuates the rise in resting tension and decrease in developed tension induced by $Ca^{2+}$ overload into myocardial cells when the heart is exposed to ischemia. (Araki, H. & Lefer, AM.: Role of prostacyclin in the preservation of ischemic myocardial tissue in the perfused cat heart. Circ. Res., 47: 757-763, 1980).

<Method>

Male Wister rats (250-350 g) were killed and their hearts perfusion with Krebs-Henseleit solution (37° C., aerated with a gas mixture of 95% $O_2$-5% $CO_2$) according to the method of Langendorff. Tension development was monitored with a force displacement transducer attached via a cotton ligature to the ventricular apex with a resting tension of 1.5 g. After a equilibration period of 1 hour, myocardial ischemia was induced by lowering perfusion pressure from 80 cm $H_2O$ to 12 cm $H_2O$ for 90 minutes. The heart was then reperfused with the previous perfusion pressure of 80 cm H2O. Rise in resting tension (g) just before reperfusion and developed tension (%) (% of value in equilibration period) 30 minutes after reperfusion were measured.

<Results>

Results are shown in Table 3.

TABLE 3

| Compound | Drug concentration (M) | Rise in resting tension (g) | Developed tension (%) |
|---|---|---|---|
| Control | — | 0.72 | 32.5 |
| 69 | $10^{-5}$ | 0.25 | 58.4 |
| 110 | $10^{-7}$ | 0.48 | 32.2 |
| 110 | $10^{-6}$ | 0.33 | 65.4 |
| 110 | $10^{-5}$ | 0.09 | 77.0 |

TEST EXAMPLE 3

Acute toxicity

Among compounds of the present invention, the compound No. 110 was tested for its acute toxicity.

<Method>

Compound No. 110 administered to male mice (18-25 g) for determination of 50% lethal dose ($LD_{50}$). Two routes of administration tested were as follows:

1) intravenous (into tail vein) administration in which calculation for $LD_{50}$ was according to up and down method and 2) oral administration in which calculation of $LD_{50}$ was according to probit method. Compound No. 110 diluted in physiological salt solution (0.9% sodium chloride) for intravenous administration and distilled water for oral administration.

Results

Results are shown in Table 4.

TABLE 4

|  | Intravenous administration | Oral administration |
|---|---|---|
| LD$_{50}$ (mg/kg) | 63 | 2800 |

What is claimed:

1. An aminobenzenesulfonic acid compound of the formula:

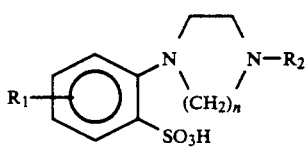

wherein $R_1$ represents hydrogen atom, a $C_1$–$C_6$ alkyl group, a $C_3$–$C_7$ cycloalkyl group, a $C_1$–$C_4$ halogenated alkyl group, a halogen atom or a $C_6$–$C_{12}$ aryl group, $R_2$ represents hydrogen atom, a $C_1$–$C_6$ alkyl group or a $C_7$–$C_{12}$ aralkyl group which may have at least one substituent selected from cyano group, nitro group, $C_1$–$C_6$ alkoxy groups, halogen atoms, $C_1$–$C_6$ alkyl groups and amino groups, and n represents an integer of 2 to 3, or a pharmaceutically acceptable salt thereof.

2. An aminobenzenesulfonic acid compound according to claim 1, wherein n is 2.

3. An aminobenzenesulfonic acid compound according to claim 1, wherein $R_2$ is hydrogen atom, $C_1$–$C_3$ alkyl group or $C_7$–$C_{12}$ aralkyl group which may be substituted by $C_1$–$C_3$ alkyl group, $C_1$–$C_3$ alkoxy group or a halogen atom.

4. An aminpbenzenesulfonic acid compound according to claim 3, wherein $R_2$ is hydrogen atom or $C_7$–$C_{12}$ aralkyl group which may be substituted by $C_1$–$C_3$ alkyl group.

5. An aminobenzenesulfonic acid compound according to claim 1, wherein $R_1$ is hydrogen atom, $C_1$–$C_6$ alkyl group, $C_5$–$C_6$ cycloalkyl group, trifluoromethyl group, a halogen atom or phenyl group.

6. An aminobezenesulfonic acid compound according to claim 5, wherein $R_1$ is $C_1$–$C_3$ alkyl group, cyclohexyl group, trifluoromethyl group, chlorine atom, bromine atom or phenyl group.

7. An aminobenzenesulfonic acid compound according to claim 1, wherein said pharmaceutically acceptable salt is a nontoxic salt selected from alkali metal salts, alkaline earth metal salts and amine salts.

8. An aminobenzenesulfonic acid compound according to claim 7, wherein said pharmaceutically acceptable salt is a nontoxic salt selected from sodium salts, potassium salts, magnesium salts, calcium salts, aluminum salts, ammonium salts, lower alkylamine salts, hydroxy lower alkylamine salts, cycloalkylamine salts, benzylamine salts and dibenzylamine salts.

9. An aminobenzenesulfonic acid compound according to claim 1, wherein said pharmaceutically acceptable salt is a nontoxic salt selected from hydrochlorides, hydrobromides, sulfates, phosphates, fumarates, succinates, oxalates and lactates.

10. An aminobenzenesulfonic acid compound according to claim 1, wherein said derivative is 2-(1-piperazinyl)-5-methylbenzenesulfonic acid or a pharmaceutically acceptable salt thereof.

11. An aminobenzenesulfonic acid compound according to claim 1, wherein said derivative is 2-(1-piperazinyl)-5-trifluoromethylbenzenesulfonic acid or a pharmaceutically acceptable salt thereof.

12. An aminobenzenesulfonic acid compound according to claim 1, wherein said derivative is 2-(1-piperazinyl)-5-n-propylbenzenesulfonic acid or a pharmaceutically acceptable salt thereof.

13. An aminobenzenesulfonic acid compound according to claim 1, wherein said derivative is 2-(1-piperazinyl)-5-phenylbenzenesulfonic acid or a pharmaceutically acceptable salt thereof.

14. An aminobenzenesulfonic acid compound according to claim 1, wherein said derivative is 2-(1-piperazinyl)-5-chlorobenzenesulfonic acid or a pharmaceutically acceptable salt thereof.

15. An aminobenzenesulfonic acid compound according to claim 1, wherein said derivative is 2-(1-piperazinyl)-5-bromobenzenesulfonic acid or a pharmaceutically acceptable salt thereof.

16. An aminobenzenesulfonic acid compound according to claim 1, wherein said derivative is 2-(1-piperazinyl)-5-iso-propylbenzenesulfonic acid or a pharmaceutically acceptable salt thereof.

17. An aminobenzenesulfonic acid compound according to claim 1, wherein said derivative is 2-(1-piperazinyl)-5-cyclohexylbenzenesulfonic acid or a pharmaceutically acceptable salt thereof.

18. An aminobenzenesulfonic acid compound according to claim 1, wherein said derivative is 2-(1-homopiperazinyl)-5-n-propylbenzenesulfonic acid or a pharmaceutically acceptable salt thereof.

19. An aminobenzenesulfonic acid compound according to claim 1, wherein said derivative is 2-[4-(2,3,4-trimethoxybenzyl)-1-piperazinyl]-5-n-propylbenzenesulfonic acid or a pharmaceutically acceptable salt thereof.

20. An aminobenzenesulfonic acid compound according to claim 1, wherein said derivative is 2-[4-(3,4-dimethoxybenzyl)-1-piperazinyl]-5-n-propylbenzenesulfonic acid or a pharmaceutically acceptable salt thereof.

21. A cardio-protective agent for ischemia-induced damage which comprises the aminobenzene sulfonic acid compound according to claim 1 as an active ingredient.

22. A composition for inhibiting Ca$^{+2}$ overload into cells of cardiac muscle or vascular smooth muscle comprising:

a Ca$^{+2}$ overload inhibitory effective amount of an aminobenzenesulfonic acid compound of the formula (I):

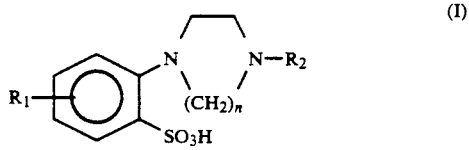

wherein $R_1$ represents hydrogen atom, a $C_1$–$C_6$ alkyl group, C $C_3$–$C_7$ cycloalkyl group, a $C_1$–$C_4$ halogenated alkyl group, a halogen atom or a $C_6$–$C_{12}$ aryl group, $R^2$ represents hydrogen atom, a $C_1$–$C_6$ alkyl group or a $C_7$–$C_{12}$ aralkyl group which may have at least one substituent selected from cyano group, nitro group, $C_1$-$C_6$ alkoxy groups, halogen atoms, $C_1$-$C_6$ alkyl groups and amino groups, and n represents an integer of 2 or 3, or a pharmaceutically acceptable salt thereof; and a pharmaceutically acceptable carrier.

23. The composition according to claim 22, wherein said aminobenzenesulfonic acid compound is present in an amount of from 1% by weight to 90% by weight based on said carrier.

24. A method of inhibiting $Ca^{2+}$ overload into cells of cardiac muscle or vascular smooth muscle in a patient in need of such treatment, comprising:

administering a $Ca^{2+}$ overload inhibitory effective amount of an aminobenzeensulfonic acid compound of the formula (I):

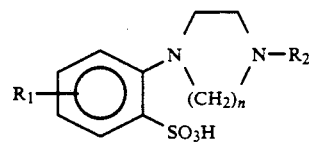

wherein $R_1$ represents hydrogen atom, a $C_1$-$C_6$ alkyl group, a $C_3$-$C_7$ cycloalkyl group, a $C_1$-$C_4$ halogenated alkyl group, a halogen atom or a $C_6$-$C_{12}$ aryl group, $R_2$ represents hydrogen atom, a $C_1$-$C_6$ alkyl group, a $C_3$-$C_7$ aralkyl group which may have at least one substituent selected from cyano group, nitro group, $C_1$-$C_6$ alkoxy groups, halogen atoms, $C_1$-$C_6$ alkyl groups and amino groups, and n represents an integer of 2 or 3, or a pharmaceutically acceptable salt thereof to said patient.

* * * * *

UNITED STATES PATENT AND TRADEMARK OFFICE
CERTIFICATE OF CORRECTION

PATENT NO. : 5,053,409
DATED : October 1, 1991
INVENTOR(S) : Hiromi Okushima et al.

It is certified that error appears in the above-identified patent and that said Letters Patent is hereby corrected as shown below:

On the title page, Item [30]:
  The second priority data has been omitted, should be, --March 15, 1990  [JP]  Japan...................2-64811--.

Signed and Sealed this

Twenty-second Day of March, 1994

Attest:

BRUCE LEHMAN

*Attesting Officer*   *Commissioner of Patents and Trademarks*